(12) United States Patent
Dasbach et al.

(10) Patent No.: US 12,233,245 B2
(45) Date of Patent: Feb. 25, 2025

(54) SHOCK ABSORBER FOR INJECTION DEVICES

(71) Applicant: SANOFI, Paris (FR)

(72) Inventors: Uwe Dasbach, Frankfurt am Main (DE); Hugo Revellat, Herts (GB); Robbie Wilson, Herts (GB); Jim Bradford, Herts (GB); Thomas Kemp, Herts (GB); William Timmis, Herts (GB); Andrew Labat-Rochccouste, Herts (GB)

(73) Assignee: Sanofi, Paris (FR)

( * ) Notice: Subject to any disclaimer, the term of this patent is extended or adjusted under 35 U.S.C. 154(b) by 451 days.

(21) Appl. No.: 17/048,007

(22) PCT Filed: Apr. 18, 2019

(86) PCT No.: PCT/EP2019/060198
§ 371 (c)(1),
(2) Date: Oct. 15, 2020

(87) PCT Pub. No.: WO2019/202130
PCT Pub. Date: Oct. 24, 2019

(65) Prior Publication Data
US 2021/0113775 A1    Apr. 22, 2021

(30) Foreign Application Priority Data
Apr. 19, 2018   (EP) .................... 18305479

(51) Int. Cl.
*A61M 5/315* (2006.01)
*A61M 5/24* (2006.01)
*A61M 5/31* (2006.01)

(52) U.S. Cl.
CPC .......... *A61M 5/31501* (2013.01); *A61M 5/24* (2013.01); *A61M 2005/2477* (2013.01);
(Continued)

(58) Field of Classification Search
CPC ................ A61M 5/31501; A61M 5/24; A61M 2005/2477; A61M 2005/3143;
(Continued)

(56) References Cited

U.S. PATENT DOCUMENTS 3,797,489 A    3/1974  Sarnoff
5,478,314 A *  12/1995 Malenchek ......... A61M 5/5066
                                                       604/110
(Continued)

FOREIGN PATENT DOCUMENTS

CN       1658919      8/2005
CN     101287514     10/2008
(Continued)

OTHER PUBLICATIONS

PCT International Preliminary Report on Patentability in International Application No. PCT/EP2019/060198, dated Oct. 20, 2020, 6 pages.
(Continued)

*Primary Examiner* — Nathan R Price
*Assistant Examiner* — Fatimata Sahra Diop
(74) *Attorney, Agent, or Firm* — Fish & Richardson P.C.

(57) ABSTRACT

The present application relates to shock absorbers for injection devices. According to a first aspect, this specification discloses an injection device including: a medicament container; a stopper translatably disposed within the medicament container; and a plunger rod including: a plunger rod body; and a shock absorber, wherein the plunger rod is operable to displace the stopper; and wherein the shock absorber contacts the stopper during displacement of the stopper by the plunger rod, thereby reducing an impact force between the plunger rod and the stopper.

19 Claims, 12 Drawing Sheets

(52) U.S. Cl.
CPC .............. *A61M 2005/3143* (2013.01); *A61M 2005/31508* (2013.01)

(58) Field of Classification Search
CPC ........... A61M 2005/31508; A61M 2005/2086; A61M 2005/3151; A61M 2205/0216; A61M 5/31515; A61M 5/20; F16F 9/3228
See application file for complete search history.

(56) References Cited

U.S. PATENT DOCUMENTS

| | | |
|---|---|---|
| 10,722,655 B2 | 7/2020 | Folk et al. |
| 2006/0178625 A1* | 8/2006 | Lim .................... A61M 5/5066 604/110 |
| 2008/0215000 A1* | 9/2008 | Barere ................. A61M 5/502 604/110 |
| 2017/0182253 A1* | 6/2017 | Folk ...................... F16F 9/3481 |
| 2017/0259002 A1 | 9/2017 | Laiosa et al. |
| 2020/0206429 A1* | 7/2020 | Hering .............. A61M 5/31501 |

FOREIGN PATENT DOCUMENTS

| | | |
|---|---|---|
| CN | 201186086 | 1/2009 |
| CN | 102327657 | 1/2012 |
| CN | 104080499 | 10/2014 |
| CN | 106413779 | 2/2017 |
| JP | 2017-518791 | 7/2017 |
| WO | WO 2003/092771 | 11/2003 |
| WO | WO 2007/019170 | 2/2007 |
| WO | WO 2011/012849 | 2/2011 |
| WO | WO 2013/057033 | 4/2013 |
| WO | WO 2015/171777 | 11/2015 |

OTHER PUBLICATIONS

PCT International Search Report and Written Opinion in International Application No. PCT/EP2019/060198, dated Jun. 27, 2019, 8 pages.

* cited by examiner

SHOCK ABSORBER FOR INJECTION DEVICES

CROSS-REFERENCE TO RELATED APPLICATIONS

The present application is the national stage entry of International Patent Application No. PCT/EP2019/060198, filed on Apr. 18, 2019, and claims priority to Application No. EP 18305479.0, filed on Apr. 19, 2018, the disclosures of which are incorporated herein by reference.

TECHNICAL FIELD

The present application relates to shock absorbers for injection devices. More particularly, the present application relates to shock absorbers for reducing the shock of a plunger contacting a stopper during an injection event.

BACKGROUND

During an injection event using an injection device, the initial contact between a plunger and a stopper in the injection device can cause a shock to the injection device. The shock may cause syringe breakage, component deformation and 'kick-back' which may affect the user experience. It may cause a user discomfort, or even result in the injection not being performed correctly. This is a particular of problem when there is an in initial gap between the plunger and the stopper, for example in under filled syringes.

SUMMARY

According to a first aspect, this specification discloses an injection device comprising: a medicament container; a stopper translatably disposed within the medicament container; and a plunger rod comprising: a plunger rod body; and a shock absorber, wherein the plunger rod is operable to displace the stopper; and wherein the shock absorber contacts the stopper during displacement of the stopper by the plunger rod, thereby reducing an impact force between the plunger rod and the stopper.

The shock absorber may be coaxial with the plunger rod body.

The shock absorber may comprise a retractable tip, the retractable tip collapsible into the plunger rod body.

The retractable tip may comprise one or more teeth engageable with a deflectable arm formed on the plunger rod body, the deflectable arm comprising one or more engaging teeth.

The one or more teeth may deflect the deflectable arm during retraction of the plunger rod tip, thereby absorbing a shock.

The deflectable arm may be formed on an outer wall of the plunger rod body.

The deflectable arm may be formed in a central bore of the plunger rod body, and the one or more teeth extend radially from the retractable tip.

An initial stopper-plunger gap may be variable by means of the retractable tip.

The retractable tip may comprise compressible protrusions that are arranged to be compressed as the retractable tip collapses into the plunger rod body.

The shock absorber may comprise: a curved recess located within the plunger rod; and a retractable tip comprising a flexible arm extending from an end plate of the retractable tip into the curved recess, wherein the curved recess is arranged to deflect the flexible arm as the retractable tip is retracted into the plunger body.

The curved recess may comprise one or more indentations and the flexible arm comprises a head, the indentations arranged to create one or more stop positions for the flexible arm as it is retracted.

The shock absorber may comprise a foam plug.

The plunger rod may comprise a sealing lip disposed between the plunger rod and the medicament cartridge, and the shock absorber comprises a venting bore in a plunger rod tip.

The shock absorber may comprise a spring mechanism.

A medicament may be stored within the medicament container. The medicament container may be a medicament cartridge.

DETAILED DESCRIPTION

Figure 1:
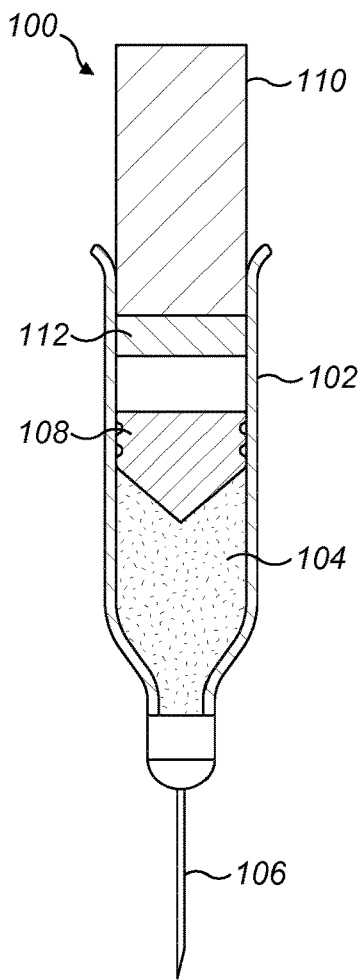
FIG. 1 shows a schematic example of an injection device with a shock absorber.

FIG. 1 shows a schematic example of an injection device with a shock absorber.

The injection device 100 comprises a medicament container 102 for retaining a medicament 104. The medicament container 102 is, in some embodiments, forms part of a syringe (for one shot devices, for example). In other embodiments, the medicament container 102 forms a part of an auto-injector. In such cases, the medicament container 102 may be a consumable part of the auto-injector capable of being replaced as required. In the embodiment shown, the walls of the medicament container 102 are substantially cylindrical. In general, the medicament container can have a different cross sectional shape. In the following description, the medicament container 102 will generally be described as a medicament cartridge. However, other examples of medicament containers 102 can alternatively be used.

The injection device 1 further comprises a needle 106 via which the medicament 104 can be expelled from the medicament cartridge 102. The needle 106 is, in some embodiments, an integral part of the medicament cartridge 102. In the following, the needle 106 end of the injection device 100 will be referred to as the distal end, with the opposite end of the injection 100 device referred to as the proximal end.

A stopper 108 is translatably disposed between the walls of the medicament cartridge 102. The stopper 108 is translatable in the axial direction of the medicament cartridge 102.

A plunger 110 (herein also referred to as a plunger rod) is provided which can be depressed into the medicament cartridge 102 in order to expel the medicament 104 via the needle 106. The plunger 110 is displaceable in the axial direction of the medicament cartridge 102. When depressed towards the distal end of the medicament cartridge 102, the plunger 110 acts to displace the stopper 108 towards the needle 106, thereby expelling the medicament 104 from the medicament cartridge 102 via the needle 106. In embodiments using an auto-injector, the plunger 110 is mounted in and/or driven by an auto-injector powerpack. The plunger 110 can also be spring driven.

A shock absorber 112 is provided on the plunger. The shock absorber 112 acts to reduce the shock of the plunger 110 contacting the stopper 108 when the plunger 110 is depressed. In the embodiment shown, the shock absorber is provided as part of the plunger 110, but in alternative embodiments it may be provided as part of the stopper 108 or as a separate component. Example embodiments of shock absorbers 112 will be described below. In some embodiments, the shock absorber is coaxial with the plunger 110.

In use, the plunger 110 is depressed towards the distal end of the medicament cartridge 102. This is done manually by a user in the case of a syringe, with the user using their fingers to depress the plunger 110. In auto-injector embodiments, the depression of the plunger 110 is achieved automatically, for example using a drive mechanism, such as a spring or motor. The drive mechanism can actuate the plunger 110 to depress the plunger 110 into the medicament cartridge.

In either type of embodiment, the depression of the plunger 110 results in the plunger 110 coming into contact with the stopper 108. Further depression of the plunger 110 will result in the stopper 108 being displaced axially along the medicament cartridge 102 towards the needle 106. This causes medicament 104 in the medicament cartridge 102 to be expelled from the needle 106.

The initial contact between the plunger 110 and the stopper 108 can result in a shock. The shock absorber 112 contacts the stopper 108 during displacement of the stopper 108 by the plunger rod 110, thereby reducing an impact force between the plunger rod 110 and the stopper 108, and hence reducing the shock. This can improve the user experience, as well as reducing syringe breakage and/or component deformation.

Figure 2A:
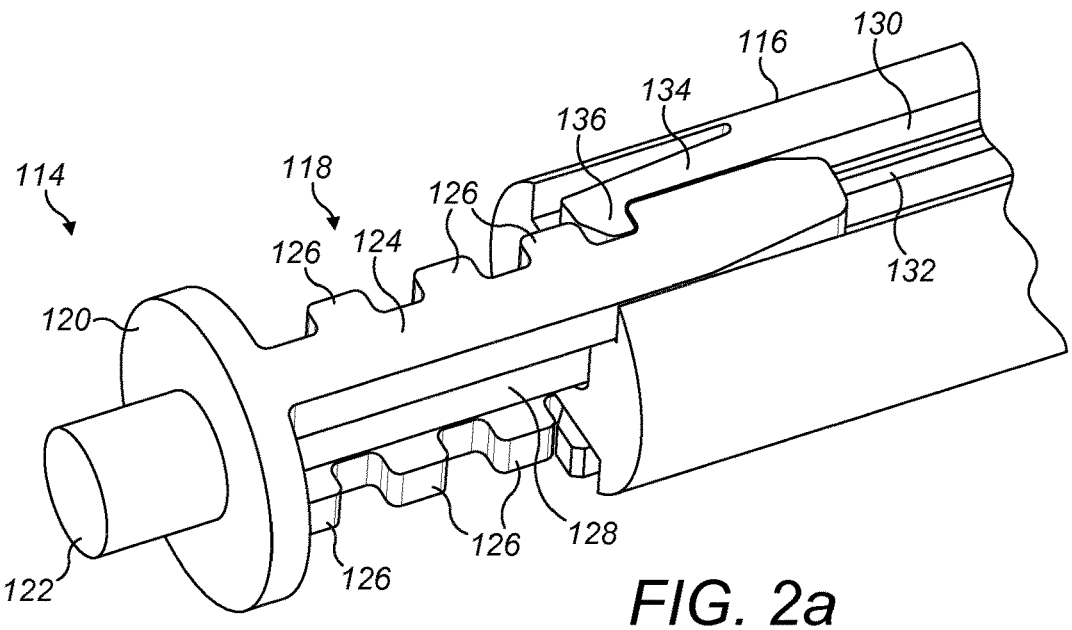
FIGS. 2a-c show an embodiment of an injection device shock absorber comprising a retractable tip.
Figure 2B:
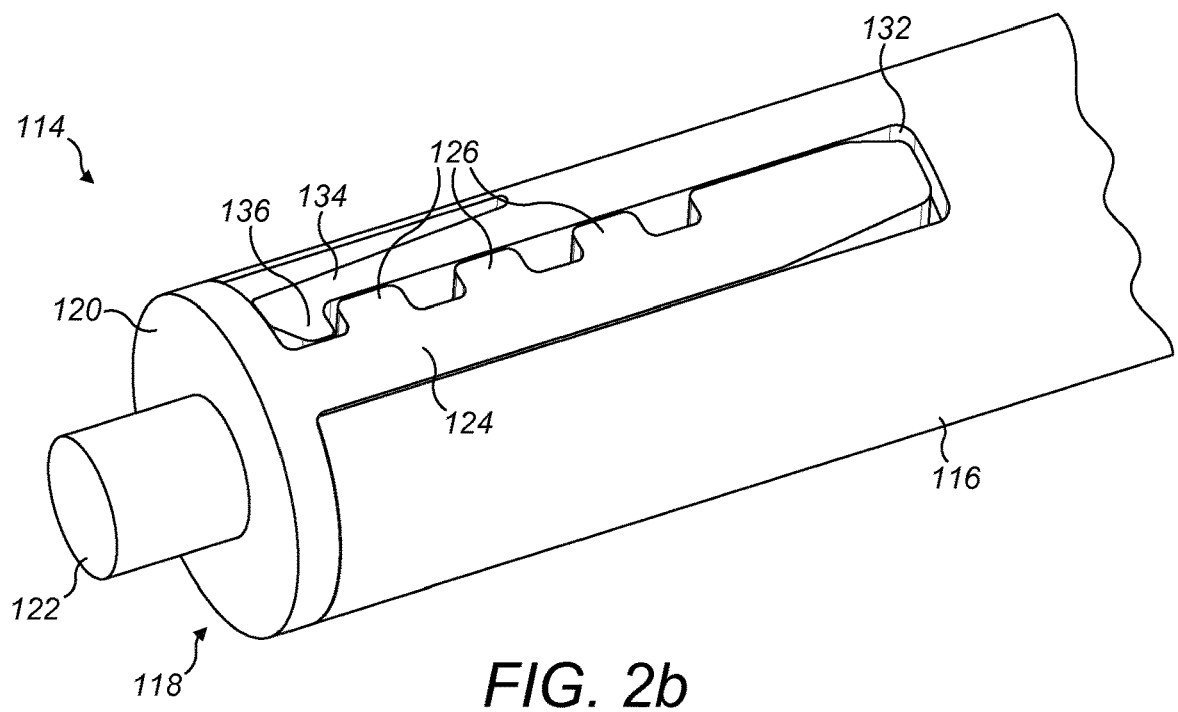
Figure 2C:
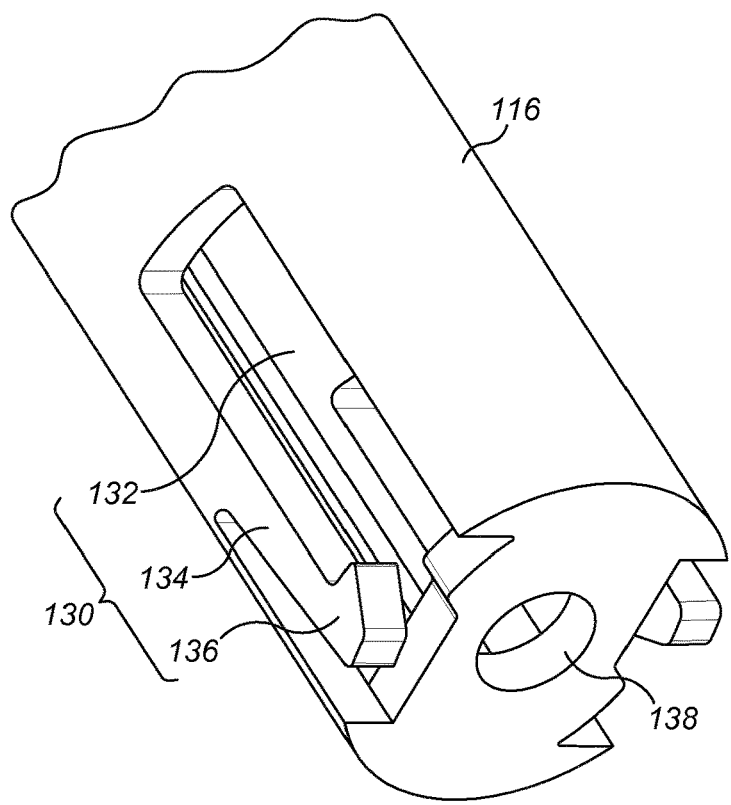
Figure 3A:
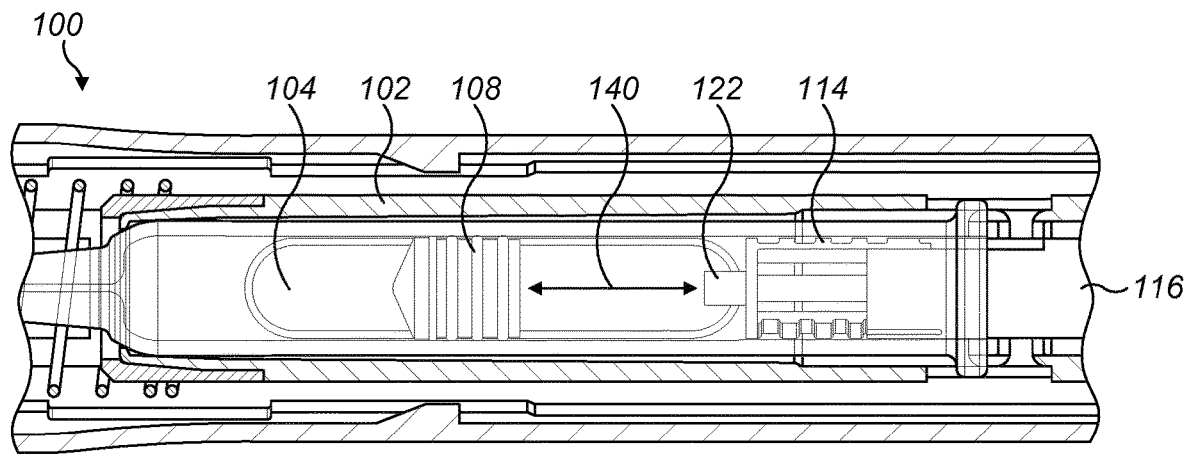
FIG. 3 shows examples of the retractable tip shock absorber in injection devices containing different medicament quantities.
Figure 3B:
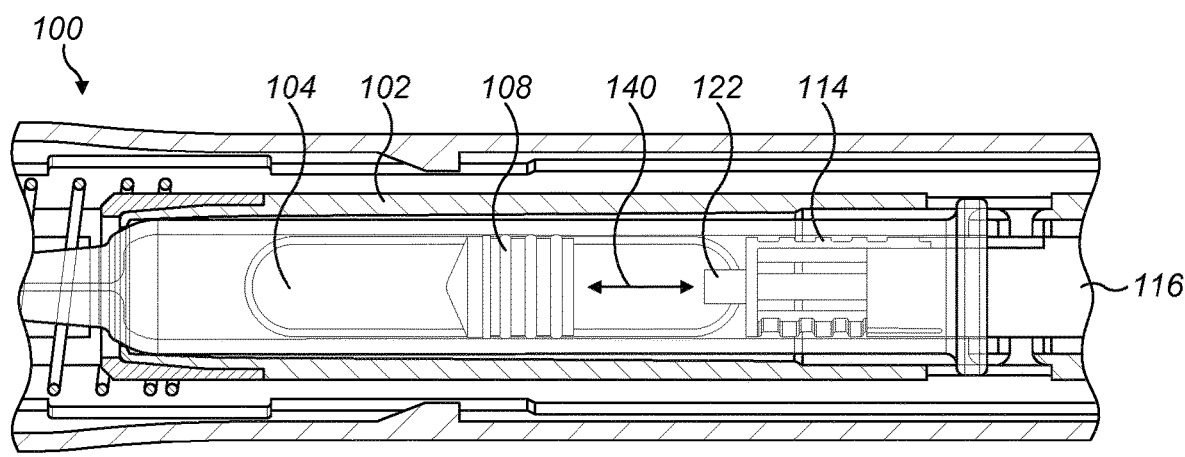
Figure 3C:
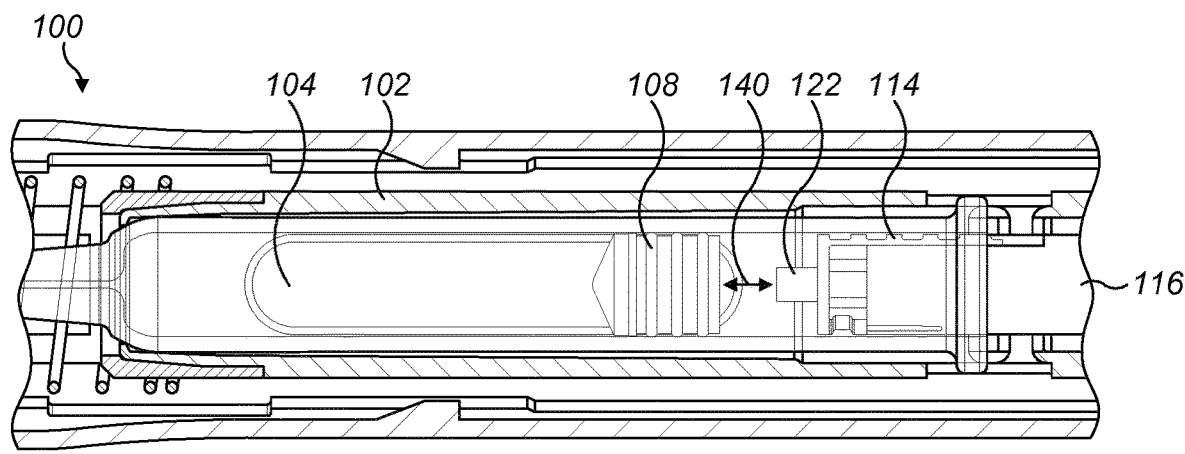
Figure 3D:
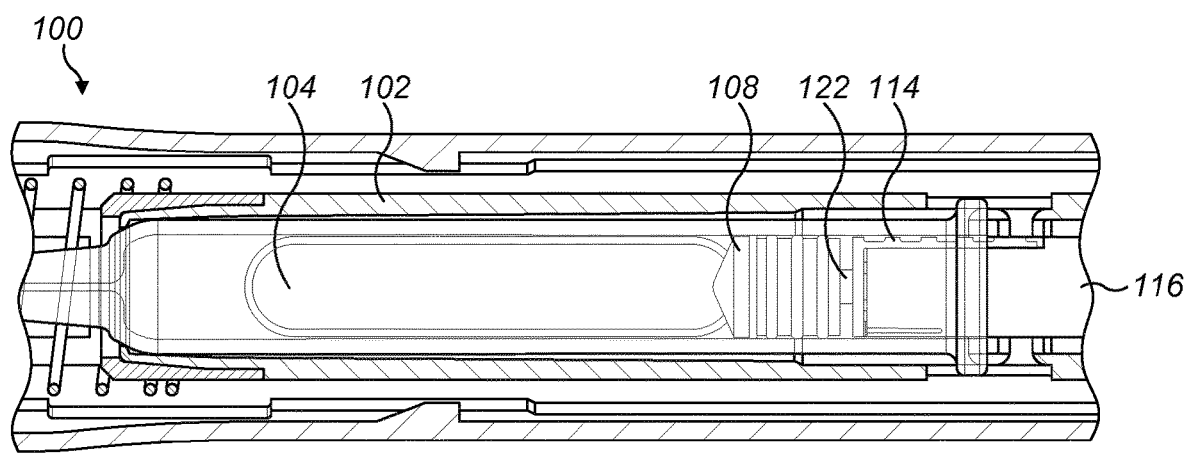

FIGS. 2a-c show an embodiment of an injection device shock absorber 112 comprising a retractable tip 114. FIG. 2a shows the retractable tip 114 in an extended configuration, while FIG. 2b shows the retractable tip 114 in a collapsed configuration. FIG. 2c shows the plunger main body 116 with the retractable tip removed.

The shock absorber 112 comprises a retractable tip 114 that is collapsible into a plunger main body 116 of the plunger 110. In the example shown, the plunger main body 116 is cylindrical, though many other shapes are possible.

The retractable tip 114 comprises a tip body 118 that is elongate in an axial direction. An end plate 120, which is in this example cylindrical, and a contact surface 122 are disposed at the distal end of the retractable tip 114. The contact surface 122 contacts the stopper 108 during operation of the plunger 110. The contact surface 122 is, in some embodiments, in the form of a protrusion from the end plate 120. However, the contact surface 122 can alternatively be formed by the end plate 120 itself.

One or more toothed beams 124 extend in the axial direction from the end plate 120 along the outside of the tip body 118 towards the proximal end of the injection device.

The toothed beams 124 each comprise one or more teeth 126. The teeth 126 can, in some embodiments (not shown), be chamfered towards the proximal end of the plunger 110. In the embodiment shown, the tip body 118 has two toothed beams 124, each disposed on an opposite side of the tip body 118 to the other.

In some embodiments, a central cylindrical rod 128 extends axially from the centre of the end plate 120. The central rod 128 can act to guide the retractable tip 114 into the main plunger body 116.

The toothed beams 124 and/or the central rod 128 can be integrally formed with the end plate 120 in some embodiments. Alternatively, the toothed beams 124 and/or the central rod 128 can be manufactured as separate components that are subsequently attached to the end plate.

The plunger main body 116 comprises one or more receiving portions 130. In the embodiment shown, two receiving portions 130 are provided, one on each of two opposing sides of the plunger main body 116. Each receiving portion comprises a groove 132 into which the toothed beams 124 of the retractable tip 114 may be received. The receiving portions 130 each comprise a deflectable arm 134 with one or more engaging teeth 136. In some embodiments, the engaging teeth 136 are chamfered towards the distal end of the plunger main body 116.

In some embodiments, the plunger main body comprises a central bore 138 into which the central cylindrical rod 128 of the retractable tip is received. The combination of the central bore 138 with the central rod 128 can act to guide the retractable tip 114 into the plunger main body 116 during its retraction.

In use, the plunger 110 is depressed axially into the medicament cartridge 102 and comes into contact with the stopper 108 via the contact surface 122 of the retractable tip 114. The retractable tip 114 is urged towards the main plunger body 116 by the resulting force on the retractable tip 114 as the friction of the stopper 108 with the medicament cartridge 102 walls is overcome. The teeth 126 of the retractable tip 114 are therefore urged against the engaging teeth 136 of the deflectable arms 134. This can cause the deflectable arm 134 to be deflected, allowing the retractable tip 114 to retract into the plunger main body 116. The deflection of the deflectable arms 134 and the friction between the retractable tip body 118 and the plunger main body 116 acts to absorb some of the shock of the impact of the plunger 110 on the stopper 108.

FIG. 3 shows examples of the retractable tip shock absorber in injection devices containing different medicament quantities.

In each example, the injection device 100 is provided with a medicament cartridge 102 filled with a different quantity of medicament 104. In the examples shown, the injection device is an autoinjector. The plunger main body 116 has a standard initial position in the injection device 100. However, the retractable tip 114 can be positioned at a different extension in dependence on the position of the stopper 108 within the medicament cartridge 102. The retractable tip 114 initial position can be varied by altering the initial number of teeth 126 that have passed the engagement teeth 136 into the plunger main body 116.

A different quantity of medicament in each medicament cartridge results in the stopper 108 being at a different initial position within each medicament cartridge 102. The retractable tip 114 can be initially positioned in order to alter the initial stopper-plunger gap 140. The initial positioning of the retractable tip 114 can be set during assembly of the injection device 100. Alternatively, it can be set during installation of the medicament cartridge 102 into the injection device 100.

Figure 4A:
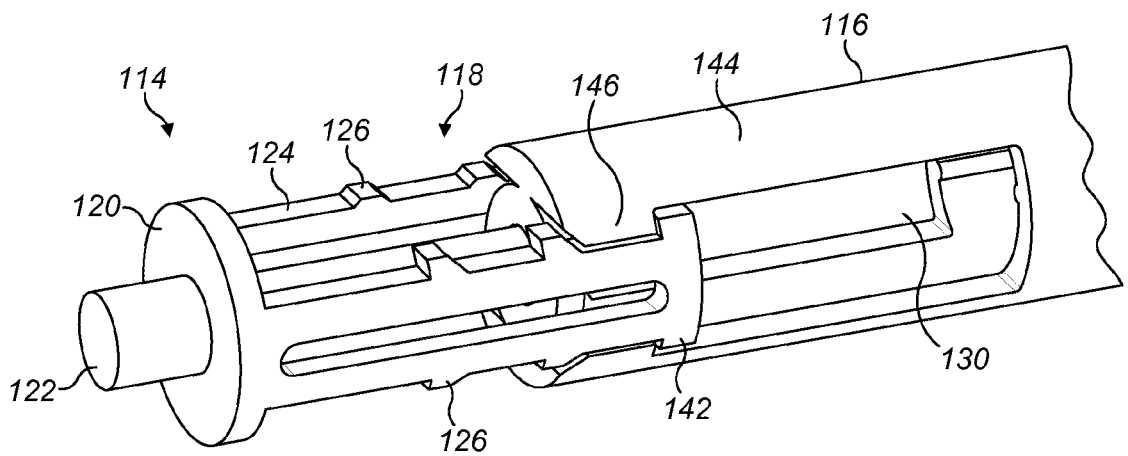
FIGS. 4a-c show an alternative embodiment of an injection device shock absorber comprising a retractable tip.
Figure 4B:
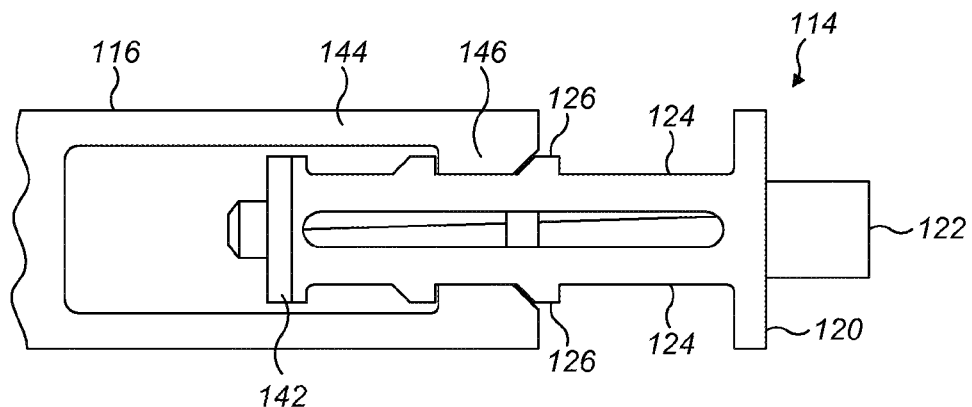
Figure 4C:
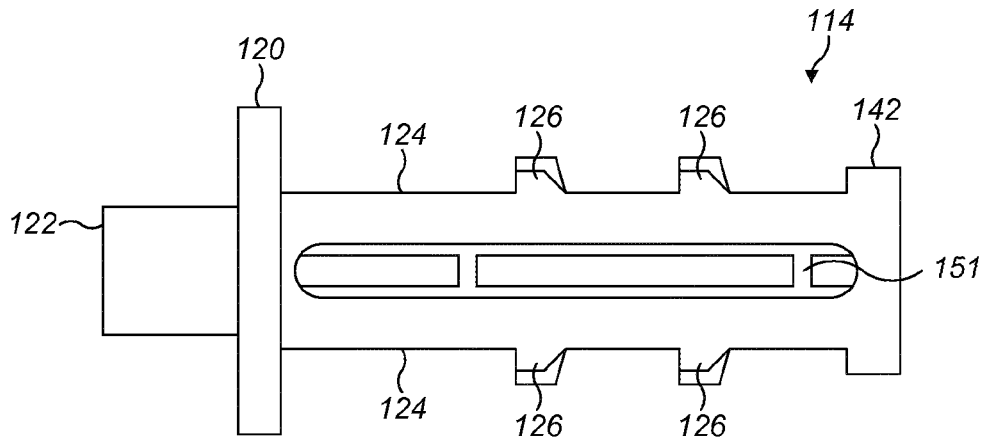

FIGS. 4a-c show an alternative embodiment of an injection device shock absorber 112 comprising a retractable tip 114. The embodiment shares many of the features of the embodiments described in relation to FIGS. 2a-c and 3a-d.

The shock absorber 112 comprises a retractable tip 114 that is collapsible into a plunger main body 116 of the plunger 110. In the example shown, the plunger main body 116 is cylindrical, though many other shapes are possible.

The retractable tip 114 comprises a tip body 118 that is elongate in an axial direction. An end plate 120, which is in this example cylindrical, and a contact surface 122 are disposed at the distal end of the retractable tip 114, as described in relation to the embodiment in FIGS. 2a-c.

One or more toothed beams 124 extend in the axial direction from the end plate 120 along the outside of the tip body 118 towards the proximal end of the injection device. The toothed beams 124 each comprise one or more teeth 126. The teeth 126 are, in the embodiments shown, chamfered towards the proximal end of the plunger 110. In the embodiment shown, the tip body 118 has two toothed beams 124, each disposed on an opposite side of the tip body 118 to the other.

The retractable tip 114 further comprises an end plate 142 for retaining the retractable tip 114 in the plunger main body 116. The plunger tip 114 can be assembled in the main plunger body 116.

In some embodiments, a central cylindrical rod 128 extends axially from the center of the end plate 120. The central rod 128 can act to guide the retractable tip 114 into the main plunger body 116.

The toothed beams 124 and/or the central rod 128 can be integrally formed with the end plate 120 in some embodiments. Alternatively, the toothed beams 124 and/or the central rod 128 can be manufactured as separate components that are subsequently attached to the end plate.

The plunger main body 116 comprises a receiving portions 130. The receiving portions 130 each comprise a stiff arm 144 with one or more engaging teeth 146. In some embodiments, the engaging teeth 146 are chamfered towards the distal end of the plunger main body 116.

In some embodiments, the plunger main body comprises a central bore 138 into which the central cylindrical rod 128 of the retractable tip is received. The combination of the central bore 138 with the central rod 128 can act to guide the retractable tip 114 into the plunger main body 116 during its retraction.

In use, the plunger 110 is depressed axially into the medicament cartridge 102 and comes into contact with the stopper 108 via the contact surface 122 of the retractable tip 114. The retractable tip 114 is urged towards the main plunger body 116 by the resulting force on the retractable tip 114 as the friction of the stopper 108 with the medicament cartridge 102 walls is overcome. The teeth 126 of the retractable tip 114 are therefore urged against the engaging teeth 146 of the arms 144. This can cause the beams 124 of the plunger tip 114 to be deflected, allowing the retractable tip 114 to retract into the plunger main body 116. The deflection of the arms 124 and the friction between the retractable tip body 118 and the plunger main body 116 acts to absorb some of the shock of the impact of the plunger 110 on the stopper 108.

The amount of damping provided by the retractable tip 114 can be varied in a number of ways. For example, the initial position of the retractable tip 114 can be varied such that one or more teeth 126 are already in the plunger main body 116, as shown for example in FIG. 4b.

Alternatively or additionally, the damping effect can be varied by changing one or more properties of the retractable tip 114, as shown for example in FIG. 4c. For example, the thickness and/or stiffness of the arms 124 can be increased or decreased. In another example, tie rods 151 can be placed between the arms 124 to limit the flexibility of the arms 124.

Properties of the teeth 126 may also be varied to vary the damping effect. For example, the height of the teeth 126 can be increased or decreased to increase or decrease the resistance to the retractable tip 114 motion respectively. The ramp angle of any chamfer on the teeth 126 can be varied. The amount of friction between the retractable tip 114 and the plunger main body 116 can be varied by altering the surface properties of one or more of the retractable tip 114 or the main plunger body 116. For example, the surface roughness of the retractable tip 114 and/or plunger main body 116 can be varied.

Material choice can be influenced by balancing several mechanical properties, for example impact resistance, toughness (such as Charpy/Izod) and flexural modulus, to select a material with the desired energy absorption properties and stiffness (to increase friction) with a sufficient resistance to fracture.

Figure 5A:
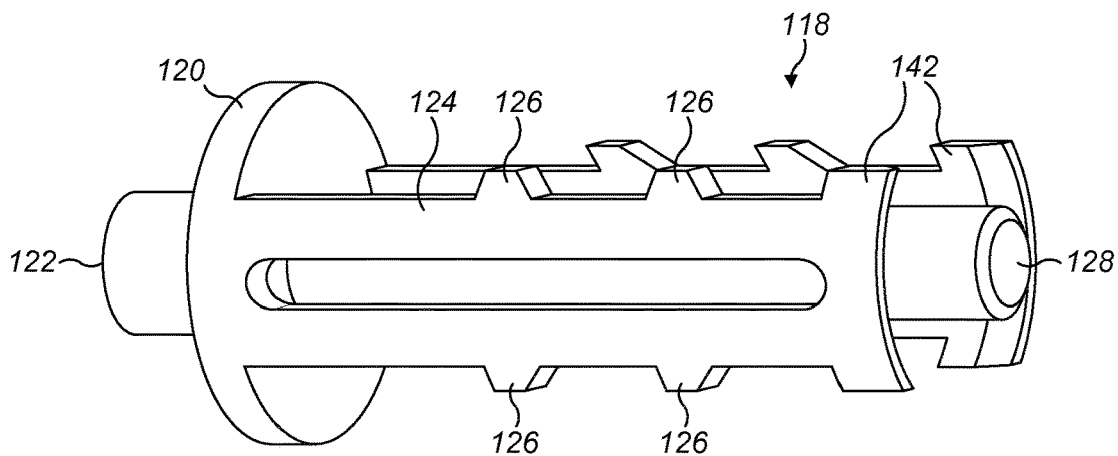
FIGS. 5a-c illustrate example embodiments of a retractable tip for a shock absorber.
Figure 5B:
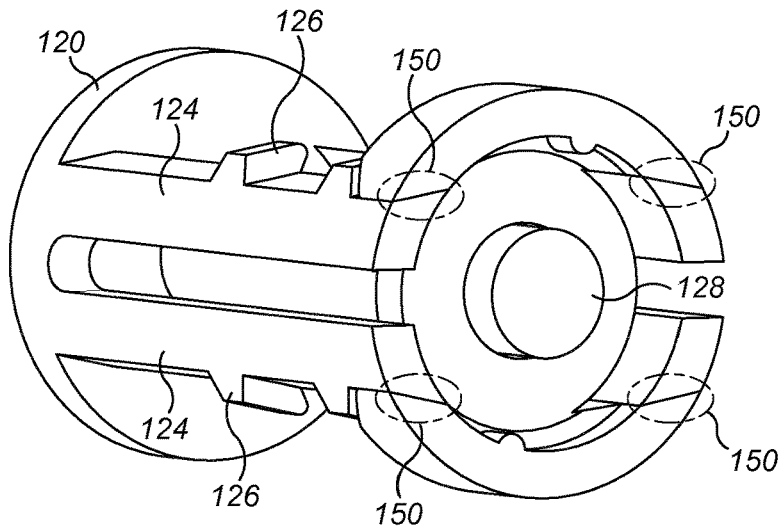
Figure 5C:
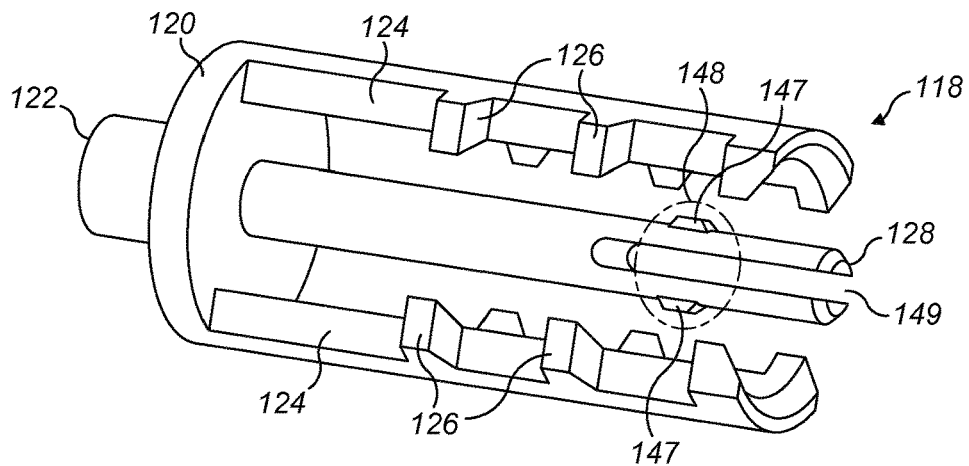

FIGS. 5a-c illustrate example embodiments of a retractable tip for a shock absorber.

FIG. 5a shows a retractable tip 114 as described in relation to FIGS. 4a-c.

FIG. 5b shows a retractable tip 114 having a retention feature 148 provided on the central rod 128. The retractable tip 114 is a variation of the retractable tip 114 described in relation to FIGS. 4a-c, with the addition of a retention feature 148 to the central rod 128. The retention feature 148 can act to retain the retractable tip 114 in the main plunger body 116 by limiting motion of the central rod 128 through the central bore 138. In the embodiment shown, the retention feature comprises two protrusions 147 from the central rod 128, though in general a plurality of protrusions 147 can be used. In some examples, the central rod 128 comprises a cut-away section 149 between the protrusions 147 that extends to the proximal end of the central rod 128. This allows for insertion of the retractable tip 114 onto the main plunger body 116.

FIG. 5c shows a retractable tip having dove-tailed tapered fits 150 between the arms 124 and the plunger slots. The retractable tip 114 is a variation of the retractable tip 114 described in relation to FIG. 4a-c. The dovetail fits 150 act to prevent radial detachment of the damper arms 124 relative to the main plunger body 116. This can improve stability, as the axial alignment angle of the arms 124 and the main plunger body 116 is more likely to be consistent. The dovetail fits 150 can also ensure that the arms of the damper remain aligned during compression, and that they do not flex outside the outer diameter of the plunger profile. Furthermore, the dovetail fits 150 can improve consistency of motion during impact.

Figure 6A:
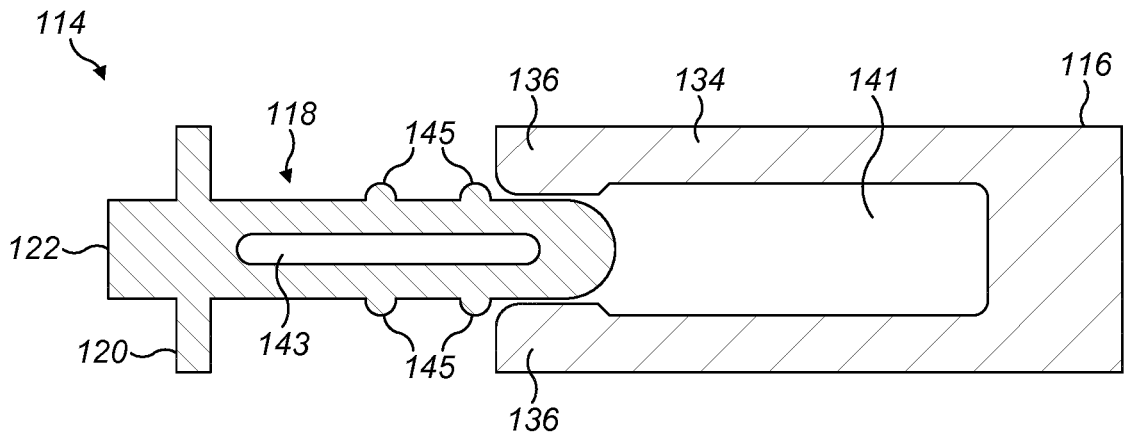
FIGS. 6a-c illustrate an alternative embodiment of a retractable tip shock absorber.
Figure 6B:
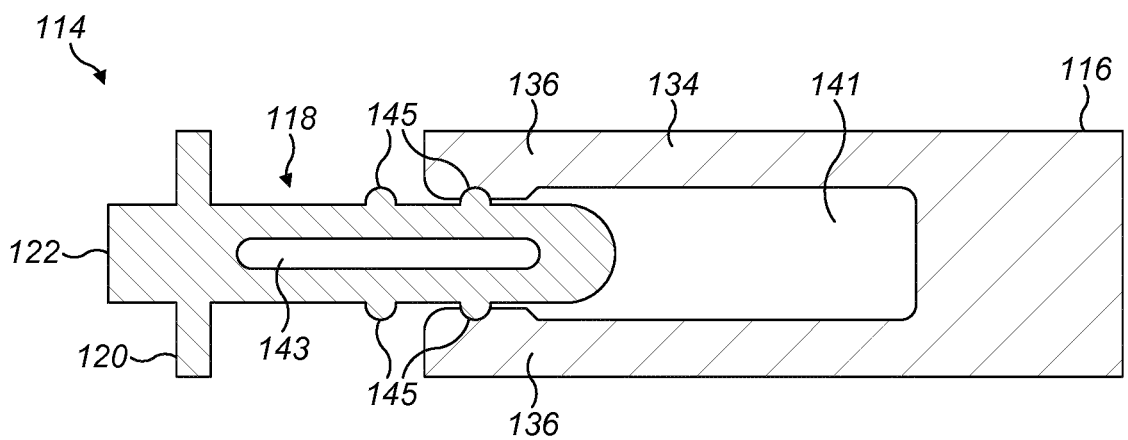
Figure 6C:
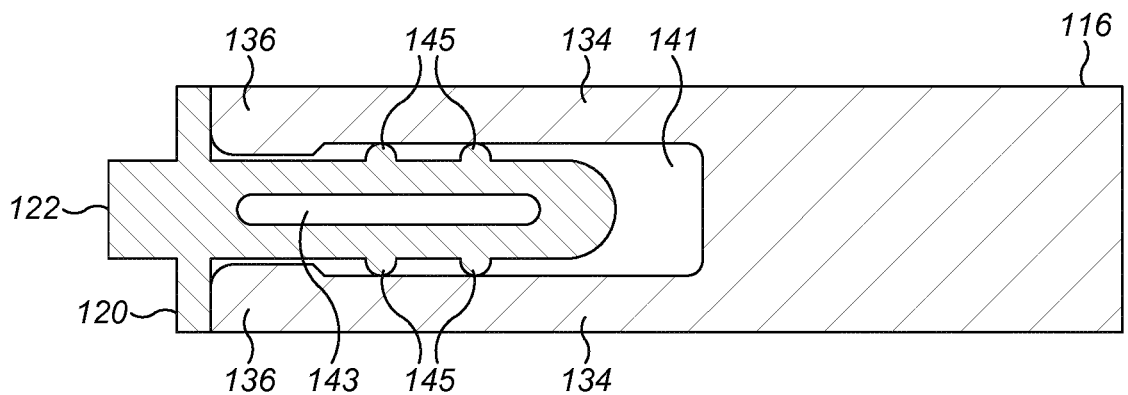

FIGS. 6a-c illustrate an alternative embodiment of a retractable tip shock absorber. FIG. 6a shows the retractable tip 114 in an extended configuration. FIG. 6b shows the retractable tip 114 in a partially retracted configuration. FIG. 6c shows the retractable tip 114 in a fully retracted configuration.

In this embodiment, the plunger is provided with deflectable side walls each comprising a deflectable arm 134 and one or more engagement teeth 136 directed inwardly into a central bore 141 of the plunger main body 116. The engagement teeth 136 are located towards the distal end of the central bore 141. The central bore receives the body 118 of a retractable tip 114.

The retractable tip 114 comprises an end plate 120 and a contact surface 122 as described above in relation to FIG. 2. A tip body 118 extends axially from the end plate 120. The tip body 118 is arranged to be received by the central bore 141 of the plunger main body 116. One or more protrusions 145 extend radially from the tip body 118. The protrusions 145 extend to a radius greater than that formed by the engagement teeth 136 in the opening of the central bore 141. In some embodiments, the tip body 118 comprises a hollow portion 143.

In use, the retractable tip 114 is urged towards the plunger main body 116 as the contact surface 122 makes contact with the stopper 108 of the injection device 100. The protrusions 145 are urged against the engagement teeth 136, causing the deflectable arm 134 to deflect outwards, allowing the retractable tip 114 to retract into the plunger main body 116. The deflection of the deflectable arms 134 and the friction between the retractable tip body 118 and the plunger main body 116 acts to absorb some of the shock of the impact of the plunger 110 on the stopper 108.

In some alternative embodiments, the deflectable arms 134 are replaced with stiffened arms, which do not deflect. Instead, the teeth 136/protrusions 145 of the retractable tip 114 are deformable, and deform as the retractable tip 114 retracts into the plunger main body 116. On impact, the teeth 136 are deformed as they pass through the opening into the plunger body 116. The material deformation absorbs the impact energy. In relation to these embodiments, the teeth 136 can also be described as compressible protrusions.

In these embodiments, the retractable tip 114 comprises a material that is tough, but has low brittleness. The degree of damping can be varied by varying the initial position of the retractable tip 114 within the plunger main body 116. Alternatively or additionally, one or more properties of the retractable tip 114 and/or plunger main body 116 can be varied, as described for example in relation to FIG. 4c.

Figure 7:
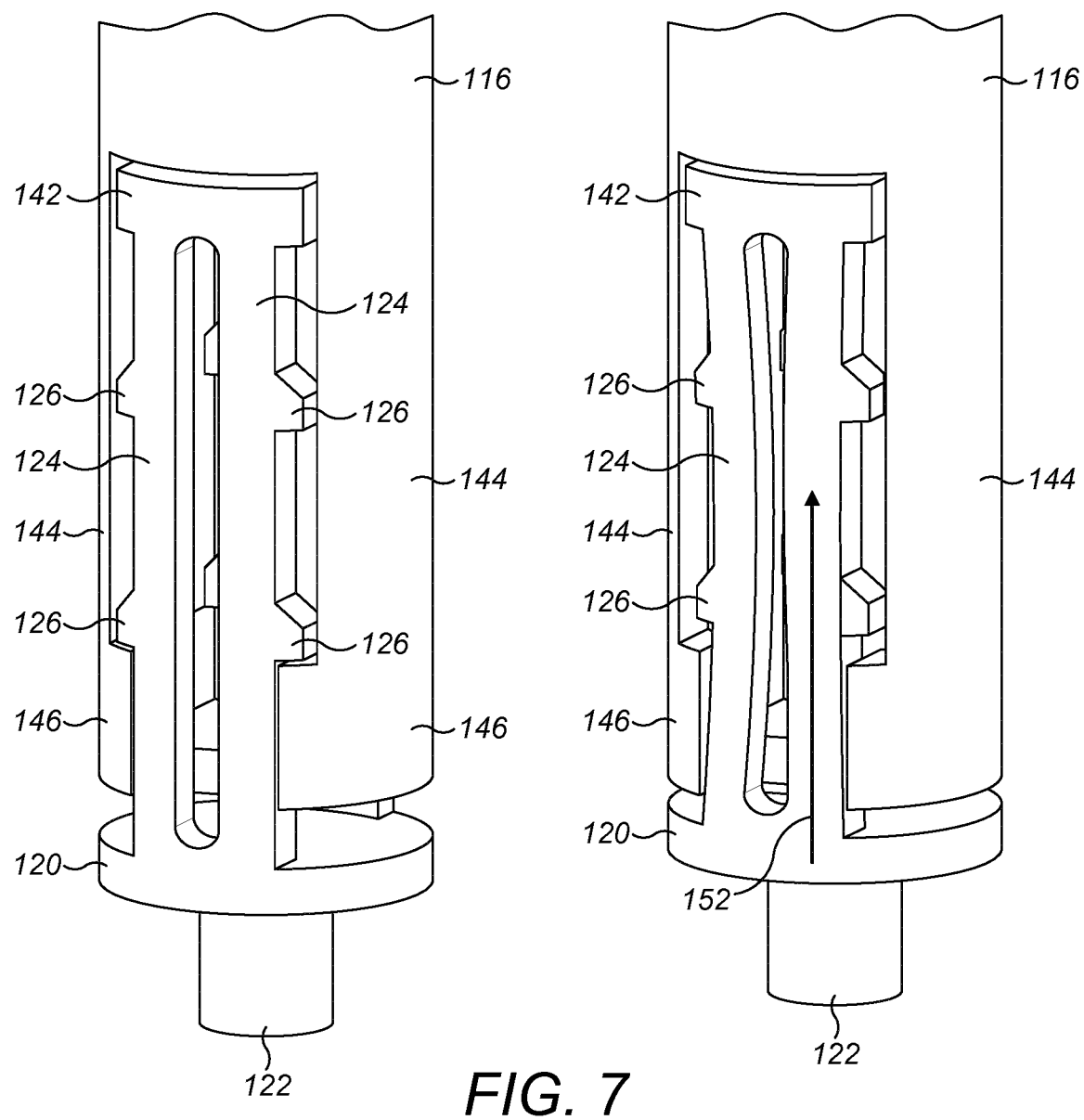
FIG. 7 shows a further example of the retractable tip being used to damp an impact force.

FIG. 7 shows a further example of the retractable tip 114 being used to damp an impact force. In this embodiment, a fully retracted tip 114 is used to further damp an impact force. The arms 124 of the retractable tip 114 can deform upon impact of the plunger 110 with the stopper 108. Under an axial load 152, the arms 124 will buckle elastically, absorbing some of the impact energy.

When the axial force is no longer applied, for example because the injection device 100 has come to the end of a dose, the retractable tip 114 arms 124 will return to their original position, as the force on the arms 124 due to the deflection is greater than the static force. This can ensure that the plunger 110 length remains consistent at end-of-dose, thereby ensuring the correct dose has been delivered.

Figure 8:
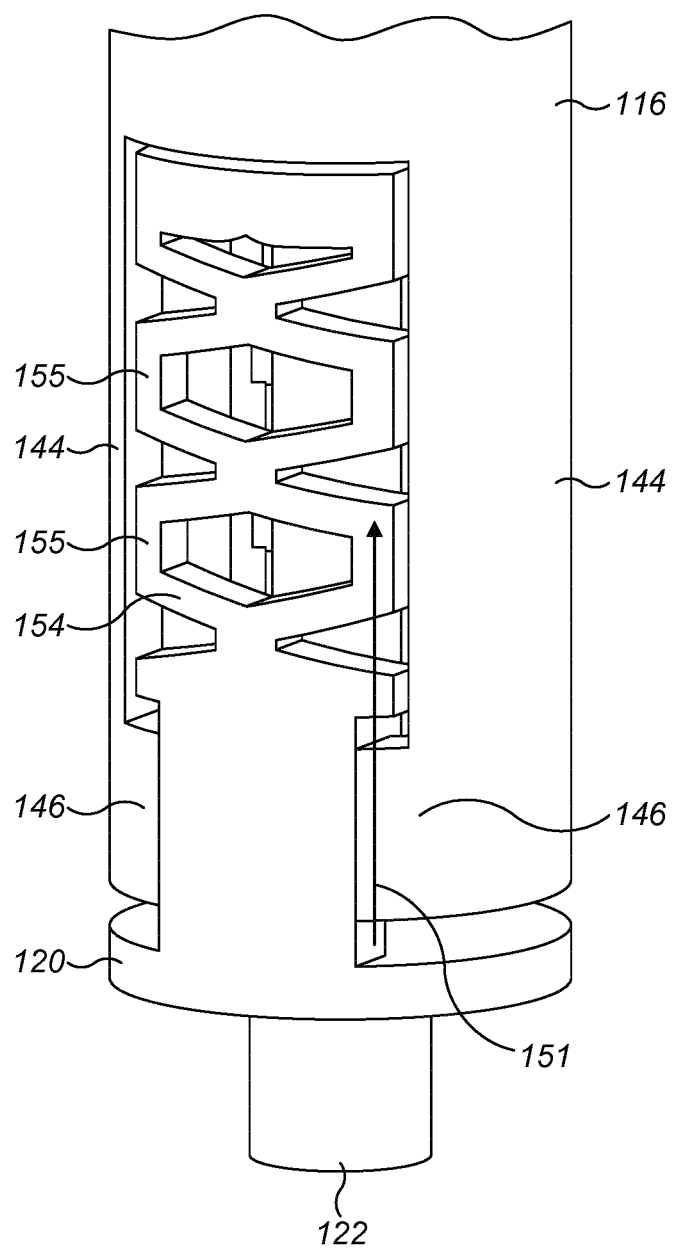
FIG. 8 shows an example of a retractable tip having a spring being used to damp an impact force.

FIG. 8 shows an example of a retractable tip 114 having a spring mechanism 154 being used to damp an impact force. In this embodiment, a fully retracted tip 114 is used to further damp an impact force. The retractable tip 114 comprises a spring mechanism 154. The spring mechanism 154 provides additional impact absorption when an axial load 152 is applied to the plunger tip 114. In the example shown, the spring mechanism 154 comprises a plurality of compressible units 155 arranged around the outside of the retractable tip 114. Other types of spring mechanism 154 can be used, for example a helical spring.

Figure 9:
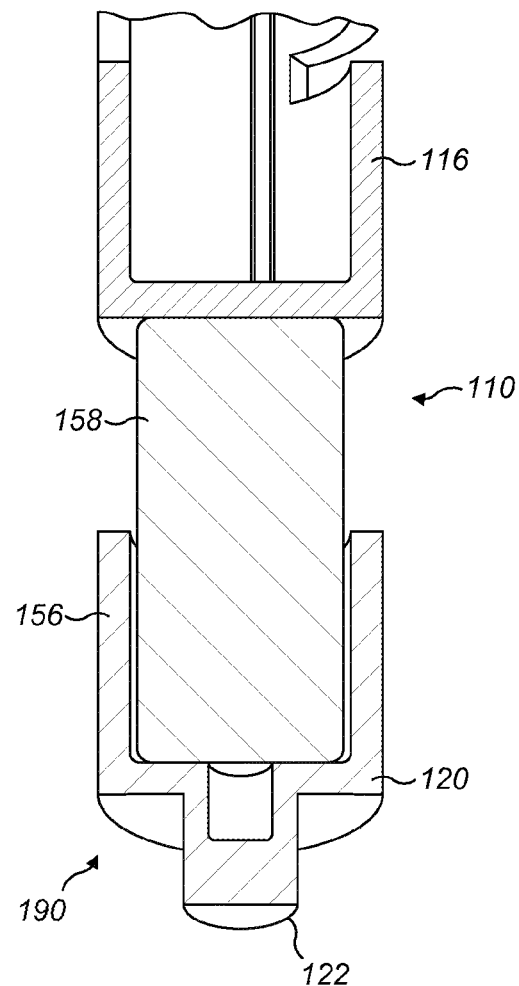
FIG. 9 shows an embodiment of an injection device shock absorber having a foam plug.

FIG. 9 shows an embodiment of an injection device shock absorber having a foam plug.

In this embodiment of the shock absorber 112, a tip 190 comprising an end plate 120 and a contact surface 122 is provided. The tip 190 further comprises side walls 156 which, together with the end plate 120, define a cavity, which in the example shown is cylindrical.

A foam plug 158 is positioned between the plunger main body 116 and the tip 190. The foam plug 158 comprises a stiff foam damper that will plastically deform on impact of the receiving tip 190 with the stopper 108. The foam plug 158 is received by the tip 190 via the cavity.

Figure 10:
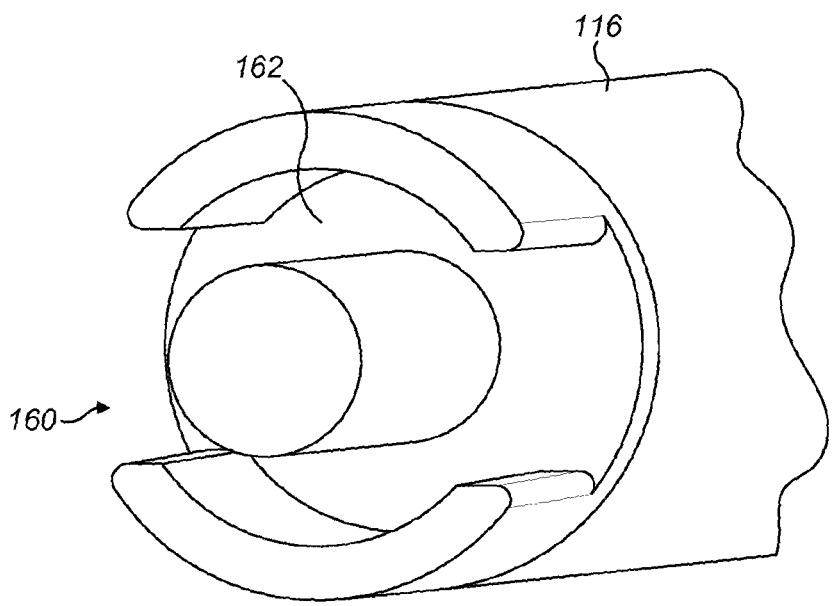
FIG. 10 shows an embodiment of a plunger main body for use with a foam plug.

FIG. 10 shows an embodiment of a plunger main body for use with a foam plug.

The plunger main body 116 comprises a main body tip 160. The main body tip 160 comprises a recess 162 to hold the foam plug 158.

Figure 11:
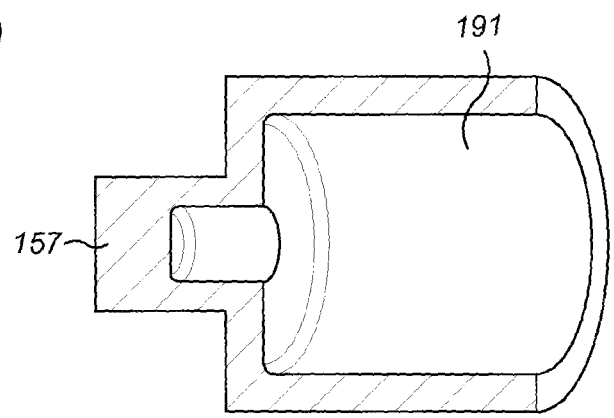
FIG. 11 shows an embodiment of a plunger tip compatible with a foam plug.

FIG. 11 shows an embodiment of a plunger tip 191. In this embodiment, the plunger tip 191 is provided with a foam tip 157 at the distal end of the plunger tip 191. The foam tip 157 comprises a stiff foam damper that will deform on impact of the plunger tip 191 with the stopper 108, thereby absorbing shock.

Figure 12:
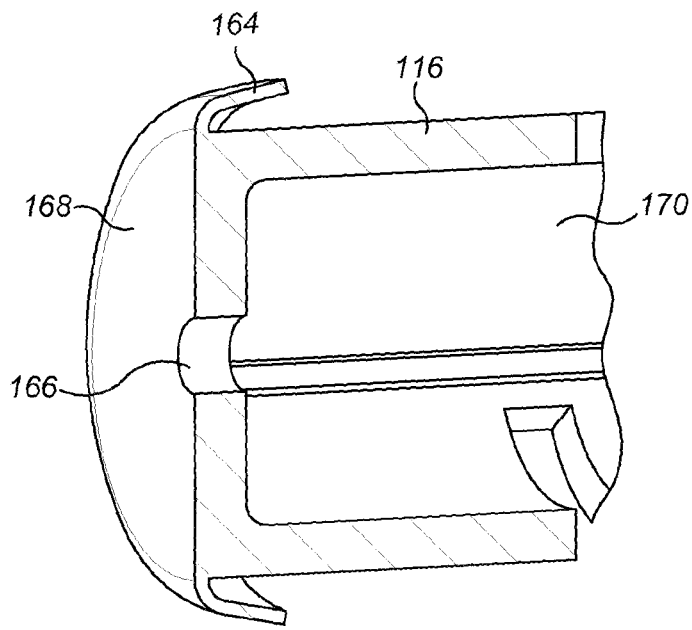
FIG. 12 shows an embodiment of an injection device shock absorber having a lip seal.

FIG. 12 shows an embodiment of an injection device shock absorber having a sealing lip.

In this embodiment of the shock absorber 112, the plunger main body 116 comprises a sealing lip 164. The sealing lip 164 extends around the circumference of the plunger main body 116. The sealing lip 164 is disposed at or near the distal end of the plunger main body 116. In use, the sealing lip 164 forms a substantially airtight seal with the barrel of the medicament cartridge.

In the example shown, the sealing lip 164 is moulded into plunger, forming an integral part of the plunger main body 116. However, the sealing lip 164 may alternatively or additionally comprise a separate flexible component attached to the plunger main body 116, for example an O-ring received by a recess in the plunger main body 116.

The plunger main body 116 further comprises a venting orifice or bore 166 on a plunger main body front plate 168. The venting orifice leads to a hollow interior 170 of the plunger main body 116, and fluidly connects the hollow interior 170 to the outside of the plunger main body 116.

In use, air in the plunger-stopper gap is compressed by the plunger main body front plate 168 as the plunger is depressed, and flows through the venting orifice 166 into the hollow interior 170 of the plunger main body 116. However, the flow of the air from the plunger-stopper gap into the hollow interior 170 is restricted by the diameter of the venting orifice 166. This causes the pressure in the plunger-stopper gap to increase, thereby acting as an air cushion to reduce the shock of the plunger 110 on the stopper 108.

Figure 13A:
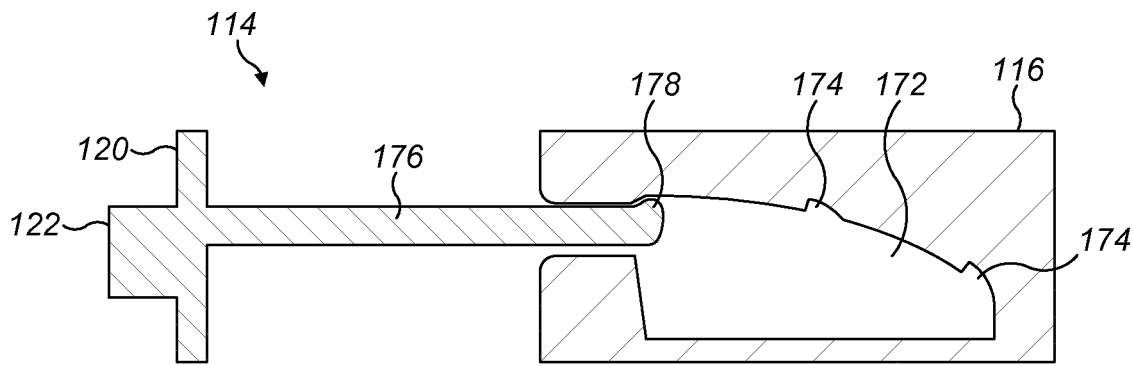
FIGS. 13a-c show an embodiment of an injection device shock absorber having a flexible arm.
Figure 13B:
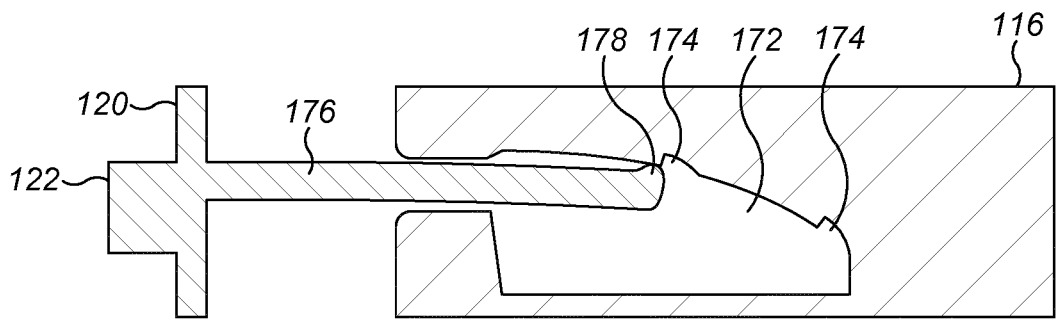
Figure 13C:
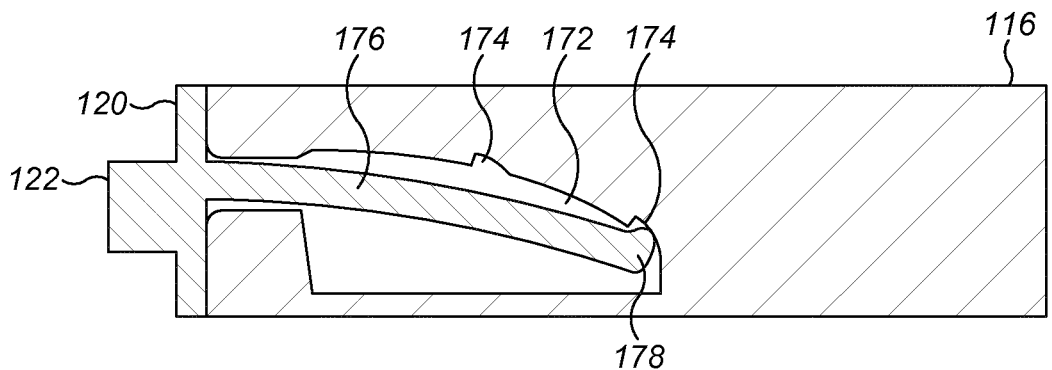

FIGS. 13a-c show an embodiment of an injection device shock absorber having a flexible arm.

In this embodiment, the plunger main body 116 comprises a curved recess 172. The curved recess 172 wall comprises one or more indentations 174. The indentations 174 are arranged to create one or more stop positions for a flexible arm 176 of a retractable tip 114 as it is retracted.

A retractable tip 114 is provided comprising an end plate 120 and a contact surface 122, as described above in relation to FIG. 2. Extending in the axial direction from the end plate 120 is a flexible arm 176. In the embodiment shown, the flexible arm 176 extends from an off centre point of the end plate 120. The flexible arm 176 terminates in a head 178 pointing in the direction of the indentations 174.

In use, the plunger 110 is depressed towards the stopper 108 in the medicament cartridge 102. As the contact surface 122 contacts the stopper 108 in the medicament cartridge 102, the retractable tip 114 is pushed into the curved recess 172, causing it to retract into the plunger main body 116. The head 178 runs along the inside of the curved recess 172 as the retractable tip is retracted, causing the flexible arm 176 to bend as the retractable tip 114 is retracted. This provides a force that resists the impact force of the plunger on the stopper.

As the head 178 runs along the inside of the curved recess 172, it will fall into the indentations 174 of the curved recess 172. The indentations 174 provide stopping points for the head 178 that create extra resistance to the impact.

It will be appreciated that one or more of the above embodiments of a shock absorber may be combined in a single injection device.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about-4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. An injection device comprising:
 a medicament container;
 a stopper translatably disposed within the medicament container; and
 a plunger rod comprising:
  a plunger rod body comprising two or more deflectable arms, each deflectable arm comprising one or more engaging teeth, and the two or more deflectable arms being integral to the plunger rod body; and
  a shock absorber comprising a retractable tip (i) collapsible into the plunger rod body and (ii) comprising two or more toothed beams, each toothed beam comprising a plurality of teeth engageable with the one or more engaging teeth of the two or more deflectable arms of the plunger rod body,
 wherein the plunger rod is operable to displace the stopper; and
 wherein the shock absorber is configured to contact the stopper such that, during displacement of the stopper by the plunger rod, the plurality of teeth of the two or more toothed beams of the shock absorber engage with the one or more engaging teeth of the two or more deflectable arms to deflect the deflectable arm, thereby reducing an impact force between the plunger rod and the stopper.

2. The injection device of claim 1, wherein the shock absorber is coaxial with the plunger rod body.

3. The injection device of claim 1, wherein the retractable tip comprises a central rod.

4. The injection device of claim 3, wherein the central rod is configured to guide the retractable tip into the plunger rod body.

5. The injection device of claim 1, wherein the plurality of teeth of the two or more toothed beams of the shock absorber are chamfered toward a proximal end of the plunger rod body.

6. The injection device of claim 1, wherein the one or more engaging teeth of the two or more deflectable arms of the plunger rod body are chamfered toward a distal end of the plunger rod body.

7. The injection device of claim 1, wherein the two or more deflectable arms are formed on an outer wall of the plunger rod body.

8. The injection device of claim 1, wherein an initial stopper-plunger gap is variable by the retractable tip.

9. The injection device of claim 1, wherein the retractable tip comprises compressible protrusions that are arranged to be compressed as the retractable tip collapses into the plunger rod body.

10. The injection device of claim 1, wherein the shock absorber comprises a foam plug disposed between shock absorber tip and a plunger main body.

11. The injection device of claim 1, wherein the plunger rod comprises a sealing lip disposed between the plunger rod and the medicament container, and the shock absorber comprises a venting bore in a plunger rod tip.

12. The injection device of claim 1, wherein the shock absorber comprises a spring mechanism.

13. The injection device of claim 1, further comprising a medicament stored within the medicament container.

14. The injection device of claim 1, wherein the two or more toothed beams of the retractable tip proximally extend from a distal end portion of the retractable tip.

15. The injection device of claim 14, wherein a first set of the plurality of teeth are disposed on a first toothed beam of the two or more toothed beams, a second set of the plurality of teeth are disposed on a second toothed beam of the two or more toothed beams, and the first set of the plurality of teeth protrude from the first toothed beam in an opposite direction relative to a direction in which the second set of the plurality of teeth protrude from the second toothed beam.

16. The injection device of claim 14, wherein the distal end portion of the retractable tip comprises a cylindrical end plate portion and the two or more toothed beams proximally extend from the cylindrical end plate portion.

17. The injection device of claim 1, wherein a distal end of each deflectable arm of the plunger rod body comprises the one or more engaging teeth.

18. The injection device of claim 17, wherein each deflectable arm of the plunger rod body extends along an axial direction of the plunger rod body.

19. The injection device of claim 18, wherein the shock absorber is configured to contact the stopper such that, during the displacement of the stopper by the plunger rod, the retractable tip moves toward the plunger rod body.

* * * * *